United States Patent
Yarin et al.

(10) Patent No.: US 6,380,858 B1
(45) Date of Patent: Apr. 30, 2002

(54) SYSTEMS AND METHODS FOR MONITORING PATIENT COMPLIANCE WITH MEDICATION REGIMENS

(75) Inventors: Paul Yarin; Richard Fletcher, both of Cambridge, MA (US); Joseph DiPisa, Wyckoff, NJ (US); Glenn Philander Vonk, Fuquay-Varina, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/929,987

(22) Filed: Aug. 15, 2001

Related U.S. Application Data

(62) Division of application No. 09/474,319, filed on Dec. 29, 1999, now Pat. No. 6,294,999.

(51) Int. Cl.[7] .............................................. G08B 23/00
(52) U.S. Cl. ..................................... 340/573.1; 128/903
(58) Field of Search ............................ 340/573.1, 10.1, 340/505, 5.92; 128/903, 899; 600/302

(56) References Cited

U.S. PATENT DOCUMENTS

| | | | | |
|---|---|---|---|---|
| 3,051,896 A | * | 8/1962 | Bieganski | .................... 600/302 |
| 3,719,183 A | * | 3/1973 | Schwartz | .................... 600/302 |
| 5,251,647 A | * | 10/1993 | Velten | .......................... 128/899 |
| 5,981,166 A | * | 11/1999 | Mandecki | ....................... 435/4 |
| 6,186,144 B1 | * | 2/2001 | Davis et al. | ............. 128/899 X |

* cited by examiner

*Primary Examiner*—Thomas Mullen
(74) *Attorney, Agent, or Firm*—Donna R. Fugit

(57) ABSTRACT

Systems and methods are provided for facilitating effective self-management of medication treatment by patients. A Smart Tray monitors and reports to third parties a patient's compliance with various medication treatment regimens. Medication containers are provided with electromagnetic tags that provide various information about medicament contained within a respective container. A Smart Tray is equipped with a processor and reader that interrogates each respective electromagnetic tag to identify medicament(s) contained within each container. Using the retrieved information, a Smart Tray provides visual and/or audio signals to a patient to remind the patient when and how much of various medicaments to take. A Smart Tray also monitors, via the reader, when a medication container is removed. A Smart Tray can communicate with one or more third parties, such as healthcare providers, pharmacies, and other suppliers of healthcare products and services via a computer network. In addition, a Smart Tray can communicate with various appliances and can modify medication regimens for particular medicaments in response to data received from various appliances.

2 Claims, 9 Drawing Sheets

SYSTEMS AND METHODS FOR MONITORING PATIENT COMPLIANCE WITH MEDICATION REGIMENS

This is a divisional of U.S. application Ser. No. 09/474,319, filed Dec. 29, 1999, now U.S. Pat. No. 6,294,999.

FIELD OF THE INVENTION

The present invention relates generally to healthcare systems and methods and, more particularly, to systems and methods for monitoring healthcare treatment.

BACKGROUND OF THE INVENTION

According to the National Medical Expenditure Survey of 1987, 90 million Americans suffer from one or more chronic conditions. Treatment of these chronic conditions represents over 76% of health care expenditures and the total direct costs of treating these chronic conditions is estimated to rise to $798 billion by the year 2030.

Many patients with chronic conditions are treated at home. Unfortunately, many patients may be unable to reliably manage their treatment, such as medication regimens, at home without the supervision of a healthcare provider. To be effective, medications often must follow various scheduling and dietary guidelines. For example, some medications are to be taken with food, others are not. Some medications are to be taken only once a day, others multiple times per day. Remembering when to take a medication and how much of it can become difficult as the number of concurrent medications increases.

Various devices for assisting patients in following medication regimens are known. For example, U.S. Pat. No. 4,837,719 to McIntosh describes a medication clock for signaling the times that dosages of a medication should be taken. The McIntosh device also provides a record of when each medicine was taken for comparison with the medication schedule. In addition, the McIntosh device can monitor and record temperature, blood pressure and pulse rate of the user.

U.S. Pat. No. 5,020,037 to Raven discloses an alarm pill box which cancels the alarm when a compartment lid is opened. A visual display is used to indicate the number of times that the lid has been opened within one day.

U.S. Pat. No. 4,911,327 to Shepherd et al., describes a dispenser for providing scheduled dosages of pills according to a predetermined medication program. A housing contains a plurality of pill containers from which dosages of pills may be released into a user-accessible pill receiver. The release of pills is controlled such that pills are released at predetermined intervals as dictated by the medication program. On release of a dosage of pills, an alarm is activated to indicate to a user that a dosage is due to be taken, the alarm being deactivated when the user accesses the pill receiver to remove the dosage of pills. If the user does not access the pill receiver within a predetermined time interval from release of the dosage, an optional remote alarm may be activated to alert a supervisor.

U.S. Pat. No. 4,616,316 to Hanpeter et al. describes a medication compliance monitoring system consisting of a blister pack having an array of plastic blisters defining compartments for medication. The blister pack has a frangible non-conductive backing sheet including conductive traces behind the compartments which are respectively ruptured when the medication doses are removed. An electronic memory circuit detects when individual compartments are ruptured and stores this information.

U.S. Pat. No. 5,408,443 to Weinberger describes a medication-dispensing system that includes a prescribing data entry station for use by a physician to store prescription information in a portable prescribing module, a dispensing data entry station for use by a pharmacy to store dispensing information in a portable dispensing data storage unit, and a medication dispenser responsive to information stored in the portable prescribing module to describe use of medication in the dispenser in accordance with a regimen prescribed by the physician and to the dispensing data storage unit to control dispensing of the medication. One embodiment has two medication drawers, each having a plurality of compartments with indicating lights selectively indicating the compartment from which medication is to be taken, a screen for displaying instructions regarding loading of the medication compartments and taking of the medication, and a keyboard including a confirming entry key for actuation by the user to confirm compliance with the instructions. Another embodiment has a series of medication-containing compartments, each covered by a separate sliding or folding cover.

U.S. Pat. No. 5,239,491 to Mucciacciaro describes a holder having a plurality of recesses for holding a plurality of medication containers, each fitting into a unique recess. The geometry of the bottom of each medication container is unique and only matches one recess in the holder. A sensor in each recess signals the presence or absence of the dedicated container to a microprocessor. The microprocessor is programmed with the prescribed dose administration schedule for each of the different medications in the different containers. A real time clock cooperates with the microprocessor and the program to signal audibly and visibly by a light at the appropriate container when a particular pill is to be administered. The signals stop when the appropriate container is removed from its recess. A different, warning sound indicates when the wrong container is lifted.

E-pill (www.epill.com) offers a pager system that sends reminders to patients to take their medication at specific times of the day. Carebridge (www.carebridge.net) provides an electronic timing device that patients can use to help them to remember to take their medication.

IBV Technologies (1500 Westlake Avenue North, Seattle, Wash. 98109) provides a medication vial that records the time a patient takes his/her medication when a button is pressed by the patient. When returned to a pharmacy for a refill, the pharmacy can download and review a compliance report from the vial and counsel the patient regarding medication compliance.

APREX (30112 Eigenbrodt Way, Union City, Calif.) provides a telemedicine service for monitoring medication compliance. Patients take their medication from medication containers outfitted with caps that have a mini-computer therein. When patients remove the cap from a bottle to take a dose of the medication contained therein, the mini-computer records the time and date of the dosing event. At the end of the day, patients place their medication bottles on a specially configured modem that transmits daily dosing information to a selected healthcare provider. If the healthcare provider detects a problem in how or when patients are taking their medication, those patients are called the next day by specially trained healthcare providers.

The MediMonitor®, available from InforMedix, Inc. (5920 Hubbard Dr., Rockville Md. 20852), is configured to retain a month's supply of up to five medications in individual compartments and alerts patients when and how to take the medications. The MediMonitor® also monitors medication use and health status by providing a date and time-stamped record of a patient's medication-taking behavior, together with patient responses to specific questions. The MediMonitor® can transmit information via an Internet-accessible server and database to clinical drug trial sites, physicians, pharmacies and other healthcare providers. Healthcare providers can communicate information, as well as reminders and specific instructions, directly to patients via the MediMonitor®.

Szeto et al. describe a holder having receptacles for five standard sized medication containers, a four-line 20-character alphanumeric LCD, and connectors for power supply and data communications. A microswitch embedded in a wall of each receptacle detects whether the receptacle is occupied or empty.

Unfortunately, existing devices for assisting patients in following medication regimens can be somewhat expensive and complex in design. Furthermore, existing devices for assisting patients in following medication regimens can seem somewhat intrusive to a user.

SUMMARY OF THE INVENTION

The present invention is directed to systems and methods for facilitating effective self-management of medication treatment by patients. A "Smart Tray" is provided that is capable of monitoring and reporting to third parties a patient's compliance with various treatment regimens, including medication regimens. Medication containers are provided with electromagnetic tags or other identifiers that provide various information about one or more medicaments contained within a respective container. A Smart Tray is equipped with a reader that interrogates each respective electromagnetic tag to identify medicament(s) contained within each container. The reader may also retrieve other information as well, such as dosage regimens. Using this retrieved information, a Smart Tray can provide visual and/or audio signals to a patient to remind the patient when and how much of one or more medicaments to take. A Smart Tray also monitors, via a reader, when a medication container is removed and stores this information. This can provide an indication of whether or not medication was taken in accordance with one or more medication regimens.

A Smart Tray according to the present invention can be configured to communicate with one or more third parties, such as healthcare providers, pharmacies, and other suppliers of healthcare products and services via a computer network such as the internet (or an intranet), a wide area network (WAN), or a local area network (LAN). For example, a Smart Tray, upon sensing that a supply of a particular medicament is low, can place an order for more of the medicament directly with a pharmacy or via a healthcare provider.

In addition, a Smart Tray can communicate with various appliances and devices including, but not limited to, personal computers, Web TVs, weight scales, refrigerators, exercise devices, and scanners. A Smart Tray can modify medication regimens for particular medicaments in response to data received from various appliances. For example, if a Smart Tray receives data from an exercise device that a patient has increased his/her exercise regimen, a processor within the Smart Tray may adjust one or more of the patient's medication regimens. In addition, data can be retrieved from various health monitoring devices, such as blood pressure monitors and the like. Retrieved data may also be utilized by a Smart Tray to modify various medication regimens.

According to another embodiment of the present invention, a Smart Tray can be configured to determine whether two or more medicaments are contraindicated. The electromagnetic tags associated with two or more medication containers can be interrogated to identify medicaments contained within the respective containers. The Smart Tray can then determine, based on information retrieved from each respective electromagnetic tag, whether or not medicaments contained within the respective containers are contraindicated. If two or more medicaments are determined to be contraindicated, a patient can be alerted by the Smart Tray. Similarly, a third party healthcare provider may be alerted by the Smart Tray.

The present invention may facilitate compliance with medication regimens, especially complex regimens involving multiple medications. As such, the present invention may reduce medication errors made by patients, such as taking the wrong drug, taking the wrong dose, taking a dose at the wrong time, or various combinations thereof. Furthermore, the present invention may reduce the need for patients to remember when and how much of a particular medication to take.

In addition, the present invention may facilitate prescription refills such that a patient receives a new prescription without a lapse in medication occurring.

DETAILED DESCRIPTION OF THE INVENTION

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout the description of the drawings.

As will be appreciated by one of skill in the art, the present invention may be embodied as methods and systems. The present invention may take the form of an entirely hardware embodiment, or an embodiment combining software and hardware aspects. Throughout the description of the present invention, the terms medicament, medicine, drug, and medication may be used interchangeably.

System Overview

Figure 1:
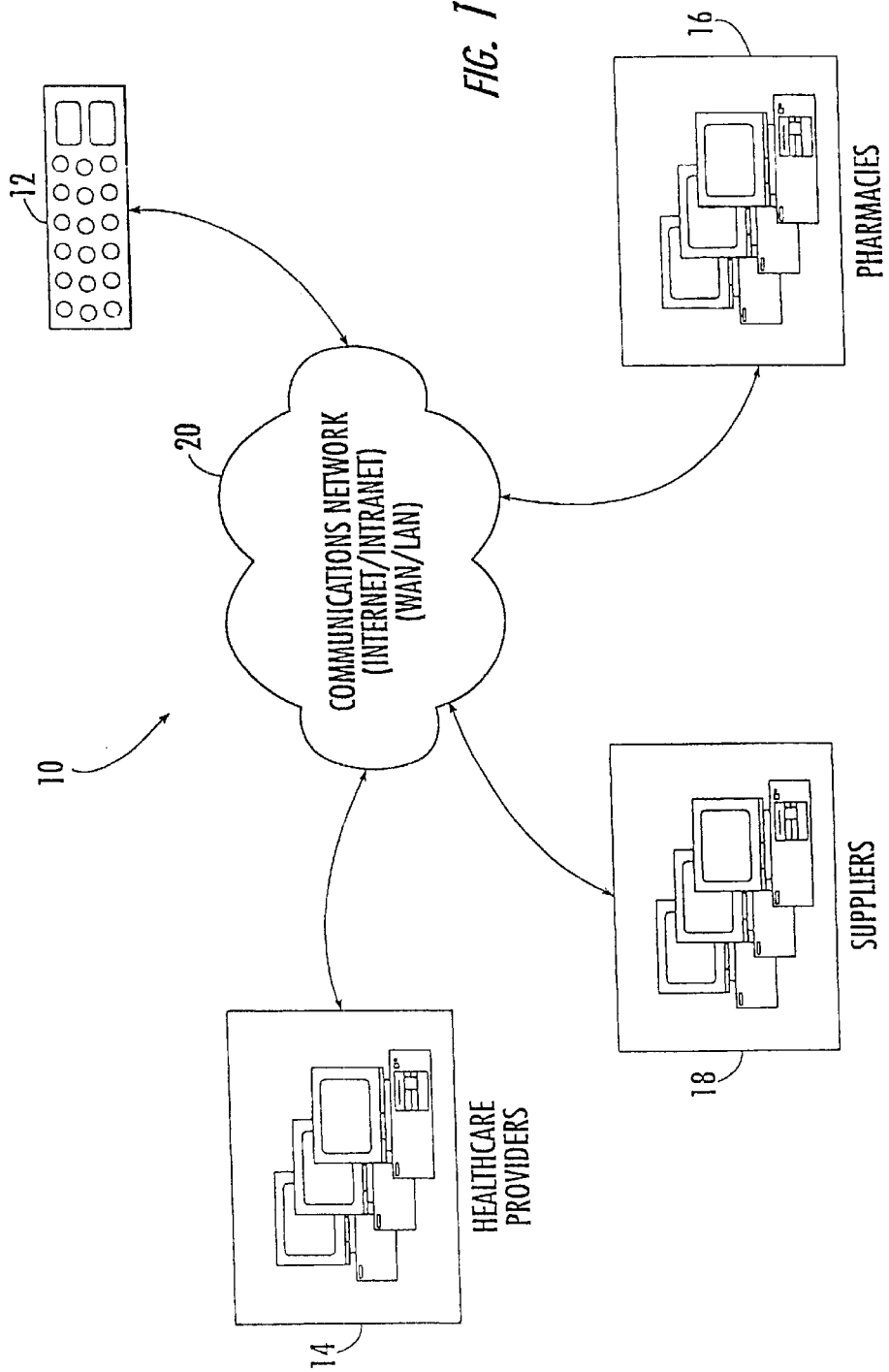
FIG. 1 schematically illustrates a system for interactively managing medication regimens of patients, according to an embodiment of the present invention.

Referring now to FIG. 1, a system 10 according to an embodiment of the present invention for facilitating effective self-management of medication treatment by patients is schematically illustrated. The illustrated system 10 includes an electronic apparatus 12, referred to as a "Smart Tray", that is capable of monitoring and reporting to third parties a patient's compliance with various treatment regimens, including medication regimens. The Smart Tray 12 can be configured to remind patients of medication they are to take at a given time of day and to record whether or not the medication was taken.

The Smart Tray 12 can also be configured to communicate with one or more third parties, such as healthcare providers 14, pharmacies 16, and other suppliers 18 of healthcare products and services via a computer network 20 such as the internet (or an intranet), a wide area network (WAN), or a local area network (LAN). The Smart Tray 12 may be configured to communicate with various data processing systems and computing devices of third parties in order to transfer and receive various information. For example, the Smart Tray 12, upon sensing that a supply of a particular medicament is low, can place an order for more of the medicament directly with a pharmacy 16 or via a healthcare provider 14. Preferably, the Smart Tray 12 utilizes a modem that is configured to communicate with external computing devices via a communications network.

Figure 2:
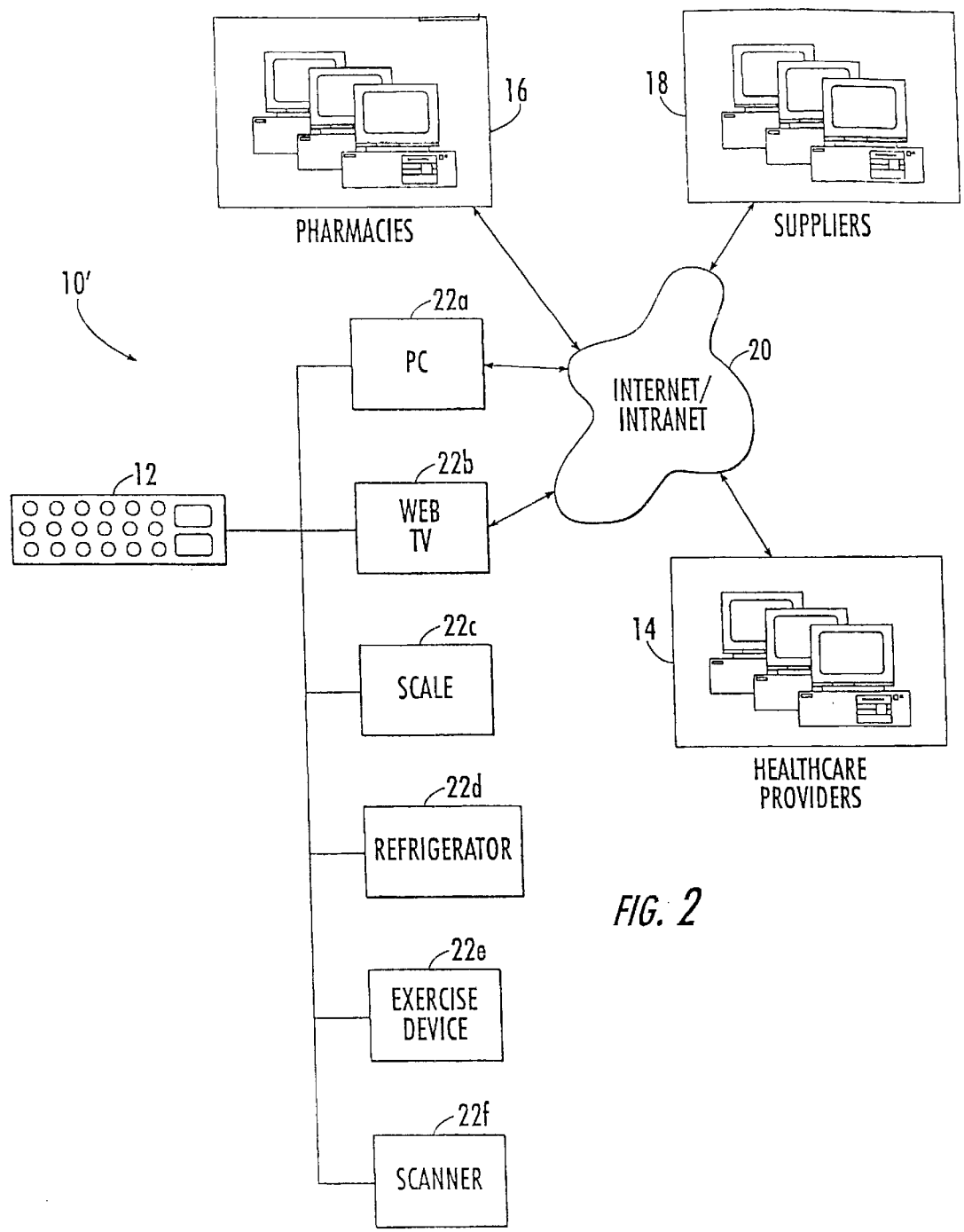
FIG. 2 schematically illustrates a system for interactively managing medication regimens of patients, according to another embodiment of the present invention wherein the Smart Tray of FIG. 1 is configured to communicate with one or more appliances and devices.

According to another embodiment of the present invention illustrated in FIG. 2, a system 10' includes a Smart Tray 12 that can communicate with various appliances (22a–22f). Exemplary appliances may include, but are not limited to, personal computers 22a, Web TVs 22b, weight scales 22c, refrigerators 22d, exercise devices 22e, and scanners 22f. The Smart Tray 12 preferably contains a processor that is configured to modify medication regimens for particular medicaments in response to data received from various appliances. For example, if the Smart Tray 12 receives data from an exercise device 22e that a patient has increased his/her exercise regimen, a processor within the Smart Tray 22 may adjust one or more of the patient's medication regimens. Similarly, medication regimens may be modified pursuant to data received from a weight scale 22c that a patient's weight has changed. A patient's food intake (as well as chemical intake, such as sodium) may also be monitored when a Smart Tray is in communication with a refrigerator 22d, or with a scanner that is configured to scan packages of food. It will be understood that although communications between the Smart Tray 12 and the other devices in FIGS. 1 and 2 are illustrated as wired communications, wireless communications also may be used.

Smart Tray

Figure 3:
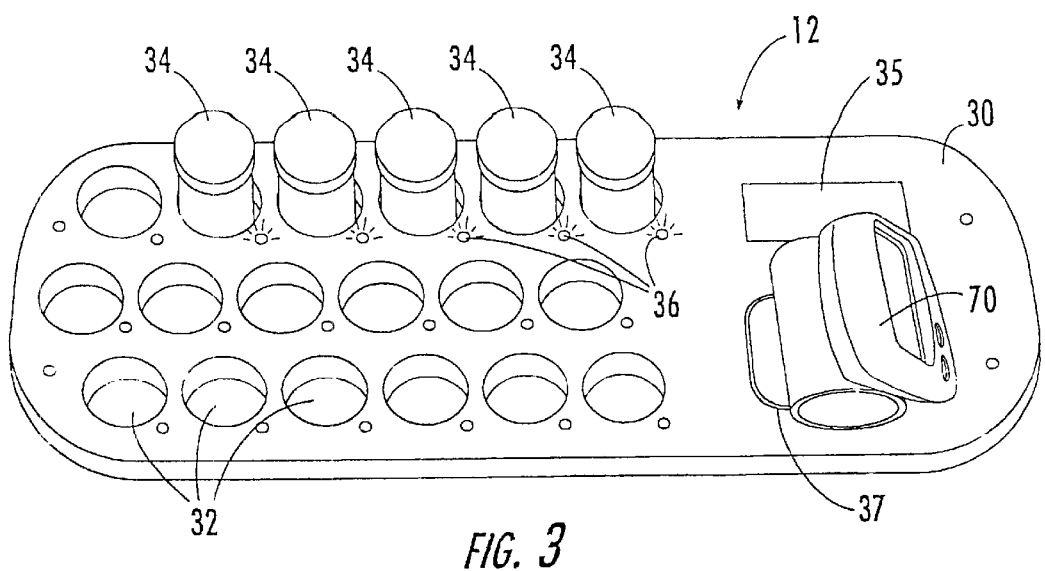
FIG. 3 is a perspective view of a Smart Tray according to one embodiment of the present invention wherein multiple medication containers are removably received within respective receptacles. In addition, a blood pressure monitor is removably received within another receptacle referred to as a sensing surface.

Referring now to FIG. 3, a Smart Tray 12, according to a preferred embodiment of the present invention is illustrated. The illustrated Smart Tray 12 has an elongated configuration with a generally flat surface 30. Disposed within the surface 30 are a plurality of receptacles 32 configured to removably receive a plurality of medication containers 34 therein. In the illustrated embodiment, the receptacles 32 have a cylindrical configuration for removably receiving cylindrical medication containers 34 (i.e., conventional pill bottles). However, it is understood that the Smart Tray 12 may have receptacles with various configurations for removably receiving medication containers of various configurations and is not limited to the illustrated embodiment. For example, custom medication containers containing "cocktails" (i.e., multiple medicaments) that are for one-time use may be utilized with a Smart Tray according to the present invention. These custom medication containers may have various shapes and sizes.

The illustrated Smart Tray 12 also includes a display 35, such as an LCD (liquid crystal display), located adjacent the plurality of receptacles 32. Various types of displays may be utilized. The Smart Tray 12 is not limited to an LCD. The display 35 is configured to display various types of information to a patient. For example, and as will be described below, when it is time for a patient to take a particular medicament, or combination of medicaments, instructions can be displayed to the patient.

The illustrated Smart Tray 12 also includes a sensing surface 37 located adjacent the plurality of receptacles 32 and display 35. As will be described below, the sensing surface 35 is a receptacle that is configured to removably receive and interact with various objects that patients may use to perform a healthcare functions. Exemplary "objects" include, but are not limited to, blood pressure monitors, thermometers, pagers, glucometers, prothrombin and coagulation monitors.

Figure 4:
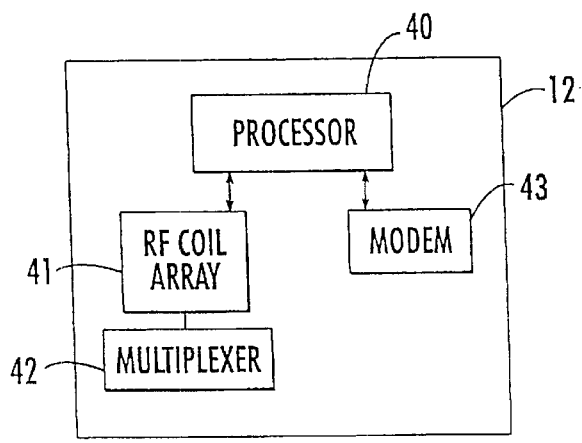
FIG. 4 schematically illustrates various electronic components included within a Smart Tray according to an embodiment of the present invention.

As illustrated schematically in FIG. 4, the Smart Tray 12 may include a processor 40. An RF coil array 41, multiplexer 42, and a modem 43 are in communication with the processor 40. The RF coil array 41 serves as an electromagnetic tag reader that can rapidly identify electromagnetic tags associated with objects disposed within a receptacle in the Smart Tray 12. The RF coils within the array 41 are switched by the multiplexer 42 in order to allow the position of multiple objects within the Smart Tray 12 to be tracked concurrently. Multiplexers are understood by those of skill in the art and need not be described further herein.

Preferably, the RF coil array 41 can identify electromagnetic tags resonating within a range of about 55 kHz to about 85 kHz. However, it is understood that electromagnetic tags resonating at other frequencies may also be identified using an RF coil array according to the present invention. Moreover, it also will be understood that various other types of identifiers may be used on the containers 34 including, but not limited to, one and two dimensional bar codes, graphical indicia, and other electronic tags. Corresponding sensors including optical, magnetic, and capacitive sensors also may be provided. Moreover, the identifiers and sensors need not be of the same type.

The processor 40 may be virtually any type of processor, such as an 8-bit processor, and controls electromagnetic tag reading and display functions. In addition, the processor 40 preferably retains a history of events within memory, as will be described in detail below. Dosage regimens for various medicaments may be stored within processor memory. In addition, dosage regimens may be read from electromagnetic tags attached to medicament containers and stored within processor memory. It will be understood that general purpose processors or special purpose processors may be used. Moreover, an Application Specific Integrated Circuit (ASIC) may be provided to integrate one or more of the elements of FIG. 4. The ASIC can include a processor and/or logic circuits to control operations.

The modem 43 is configured to communicate with external computing devices so that data stored within processor memory can be transmitted to healthcare providers and other third parties, including medicament suppliers (e.g., pharmacies), and so that information can be received from healthcare providers and other third parties.

In the embodiment of FIG. 4, each RF coil within the array 41 is associated with (and is preferably positioned adjacent to) a respective receptacle 32. An RF coil in the array 41 is also associated with (and positioned adjacent to) the sensing surface 37. Each RF coil is configured to independently sense the presence of an object having an electromagnetic tag, such as a radio frequency identification (RFID) tag, secured thereto. For example, an RF coil associated with a particular receptacle 32 can sense the presence of an object having an electromagnetic tag disposed within the receptacle. It will also be understood that one RF coil can sense multiple RFID tags on one or more containers. As such, one RF coil may be utilized for more than one receptacle 32.

In addition, each RF coil in the array 41 is configured to communicate with an electromagnetic tag attached to an object in the vicinity of the RF coil. Preferably, each RF coil serves as a "reader" that can "interrogate" an electromagnetic tag (or other identifier) to obtain information stored within the electromagnetic tag (or other identifier). When attached to a medication container, an electromagnetic tag may contain information that identifies one or more medicaments contained within the container, and information about dosage rates and frequency of dosages. Other information relevant to a patient's treatment may also be stored within an electromagnetic tag. For example, information about whether a medicament needs to be taken with food, whether a patient should avoid sunlight may be included, and other similar types of information may be included. Information obtained from an electromagnetic tag by an RF coil may be stored within the processor memory.

RF coils and their use in detecting the proximity of electromagnetic tags and for interrogating electromagnetic tags for information are understood by those of skill in the art and need not be discussed further herein. A particularly preferred Smart Tray having an array of RF coils for detecting the proximity of objects tagged with electromagnetic tags and for interrogating electromagnetic tags for information is disclosed in a co-assigned and co-pending U.S. Provisional Application, entitled Platform for Item Sensing and Identification, Ser. No. 60/173,605, which was filed Dec. 29, 1999, and which is incorporated herein by reference, in its entirety.

RFID tags typically contain circuitry that stores and transmits information about the item attached to the tag in cooperation with a compatible RFID reader/writer. Conventional RFID circuitry does not require a battery or an external energy source. However, a battery may be included. RF energy is typically transmitted by an RF reader specifically adapted to interact with the RF circuitry of an RFID tag. RFID tags are described in U.S. Pat. No. 5,528,222 which is incorporated herein by reference in its entirety.

Figure 5:
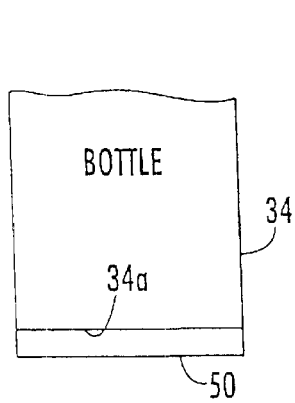
FIG. 5 is a side elevation view of an exemplary medication container having an RFID tag affixed to a bottom surface thereof.

Referring now to FIG. 5, an exemplary medication container 34 has an RFID tag 50 affixed to the bottom surface 34a thereof. An RF coil (39, FIG. 6) associated with a respective receptacle 32 is configured to detect the presence of a medicine container 34 disposed therein via the RFID tag 50. In addition, an RF coil is also configured to interrogate the circuitry of the RFID tag 50 to obtain information therefrom. Although the illustrated RFID tag 50 is attached to the bottom surface 34a of the medicine container, it is understood that RFID tags can be attached to (or incorporated within) medication containers in various locations, and the RF coil may be located at various locations.

Referring back to FIG. 3, the illustrated Smart Tray 12 includes an LED (light emitting diode) 36 adjacent each respective receptacle 32. Each LED 36 serves as a visual indicator for displaying visual signals to a patient. For example, when a medication container 34 is placed within a respective receptacle 32, the LED 36 adjacent the receptacle 32 may display a green color. When a medicament within a medication container 34 disposed within a receptacle 32 is to be taken by a patient, the LED 36 may display a red color, or may flash in order to gain the attention of the patient. In the illustrated embodiment of FIG. 3, five medication containers 34 are disposed within five respective receptacles 32. An LED 36 adjacent each of these receptacles is illuminated to indicate the presence of a medication container therewithin.

In addition, the Smart Tray 12 may include an audio indicator that can audibly signal a patient as to which medications should be taken in accordance with a medication regimen. Exemplary audio signals may include, but are not limited to, voice commands and signals such as bells, whistles, beepers, buzzers, and the like.

The number of flashes and/or audio signals can be used to indicate the number of pills (dosage amount) to be taken. For example, three flashes (or audio signals) can indicate three pills, two flashes (or audio signals) can indicate two pills, and so forth. In addition, voice commands may also be utilized to specify medicament quantity.

Each time a tagged medication container 34 is placed within a receptacle 32, or a tagged object is placed on the sensing surface 37, the event is recorded by a processor 40 or other device within the Smart Tray 12. Similarly, each time a medication container 34 is removed from a receptacle 32, or an object is removed from the sensing surface 37, the removal event is recorded by the Smart Tray processor 40 or other device. Each event is stored and can be communicated to other computing devices via a communications network 20.

The Smart Tray 12 may be configured to communicate with computing devices via communications networks that conform to various standards and protocols including, but not limited to, the Bluetooth standard. As is well known to those having skill in the art, Bluetooth technology provides a universal radio interface in the 2.45 GHz frequency band that enables portable electronic devices to connect and communicate wirelessly via short-range ad hoc networks. Bluetooth technology is described for example in Haartsen, "Bluetooth-The Universal Radio Interface for Ad Hoc, Wireless Connectivity", Ericsson Review No. 3, 1998, pp.

110–117, the disclosure of which is hereby incorporated herein by reference. In addition, a serial data connection may be provided to allow the exchange of data with external appliances and other devices.

When a medication container 34 is placed within a receptacle 32, an RF coil associated with the receptacle 32 can interrogate an RFID tag 50 attached to the medication container to obtain information about the medicament(s) within the container 34. Exemplary information includes the name of the medicament(s) and a dosage regimen for the medicament(S). A dosage regimen typically includes an amount of a medicament and time(s) that each dose is to be taken. In addition, other information, such as whether to take a medication with food, or whether to avoid taking a medicament in conjunction with other types of medications, can also be retrieved from an RFID tag. Preferably, a Smart Tray 12 according to the present invention can display various types of information to a patient via the display 35.

Figure 6:
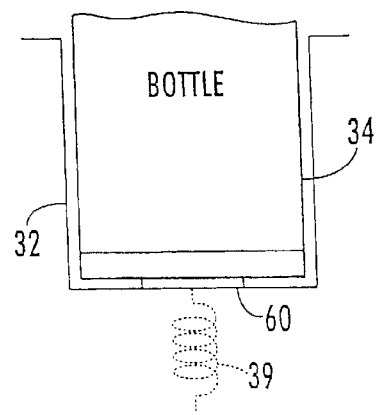
FIG. 6 is a side elevation view of an exemplary medication container having an RFID tag affixed to a bottom surface thereof and having a piezoelectric element affixed to, and in communication with, the RFID tag.

According to another embodiment of the present invention illustrated in FIG. 6, one or more piezoelectric elements 60 or other weighing devices may be attached to a medicine container 34. In the illustrated embodiment, a piezoelectric element 60 is attached to an RFID tag 50 on the bottom surface 34a of a medication container 34. As is understood by those of skill in the art, piezoelectric elements generate an electrical signal when a mechanical stress is applied thereto. Accordingly, by measuring an electrical signal generated by a piezoelectric element 60 stressed under the weight of the medicine container 34, the weight (and, thus, the amount) of medicament within the medication container 34 can be determined. By using piezoelectric elements, a Smart Tray 12 according to the present invention can monitor how much of a medicament has been taken over time, thereby facilitating monitoring user compliance with medication regimens. Piezoelectric elements according to this aspect of the present invention can communicate with an RFID tag attached to a medication container (or other object) or can communicate directly with an RF coil or other sensor within the Smart Tray 12.

Referring back to FIG. 3, a blood pressure monitor 70 is disposed on the sensing surface 37. An RF coil associated with the sensing surface 37 preferably communicates with an electromagnetic tag (not shown) attached to the blood pressure monitor 70 and downloads information therefrom. For example, after measuring his/her blood pressure with the blood pressure monitor 70, a patient can place the blood pressure monitor 70 on the sensing surface 37 and blood pressure information can be downloaded to and stored within the Smart Tray processor 40. This information may be transmitted to a third party healthcare provider via modem 43. Alternatively, this information may be used to modify one or more dosage regimens for one or more medicaments as described above.

The sensing surface 37 may be used to download information from virtually any type of healthcare device having an electromagnetic tag attached thereto or embedded therewithin that a patient may use including, but not limited to, blood pressure monitors, thermometers, pagers, glucometers, prothrombin and coagulation monitors.

A Smart Tray according to the present invention passively and unobtrusively facilitates monitoring patient compliance with medication treatment regimens. For example, the Smart Tray can remind patients which medication to take using visual and/or audio cues. In addition, the Smart Tray can record medication administration as an aid to disease management. Furthermore, the Smart Tray can facilitate disease management by providing education and motivation to patients.

A Smart Tray according to the present invention also can facilitate control over medicament inventory by automatically placing orders prior to supply depletion. A Smart Tray can be incorporated into a medicine cabinet or shelf, and can be integrated with kitchen shelf for both diet and medication management. A Smart Tray may be utilized with various medicine-dispensing regimens. For example, the Smart Tray can be utilized with dispensers of liquid medicines. A Smart Tray may also be incorporated within a refrigeration device. A portable version of a Smart Tray may be configured for travel.

According to another embodiment of the present invention, a Smart Tray can be configured to alert patients if one or more medicaments are contraindicated. As is known to those of skill in the art, the term "contraindicated" means that when administered together, two or more medicaments may cause an adverse reaction in a patient or can inhibit the effectiveness of each other. Contraindications may be signaled via a visual indicator or via an audio indicator, or some combination of audio and visual indicators.

Figure 13:
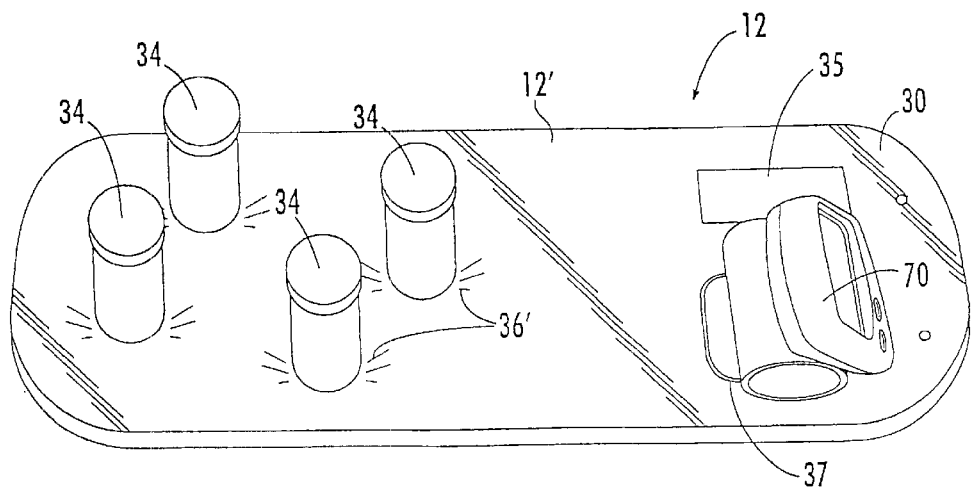
FIG. 13 is a perspective view of a Smart Tray according to another embodiment of the present invention wherein receptacles are not utilized and wherein visual indication of the presence of an object is utilized.

A Smart Tray according to the present invention need not have receptacles for receiving medication containers and other objects. For example, as illustrated in FIG. 13, a Smart Tray 12' may have a generally flat surface 30 for receiving tagged objects such as medication containers 34. An RF coil array can be configured to recognize a tagged object placed anywhere on the surface 30. Various types of visual indicators may be utilized to indicate the presence of a tagged object. In the illustrated embodiment, portions 36' of the surface directly beneath a tagged medication container 34 are illuminated to indicate the presence of the tagged medication containers 34.

Operations

Figure 7:
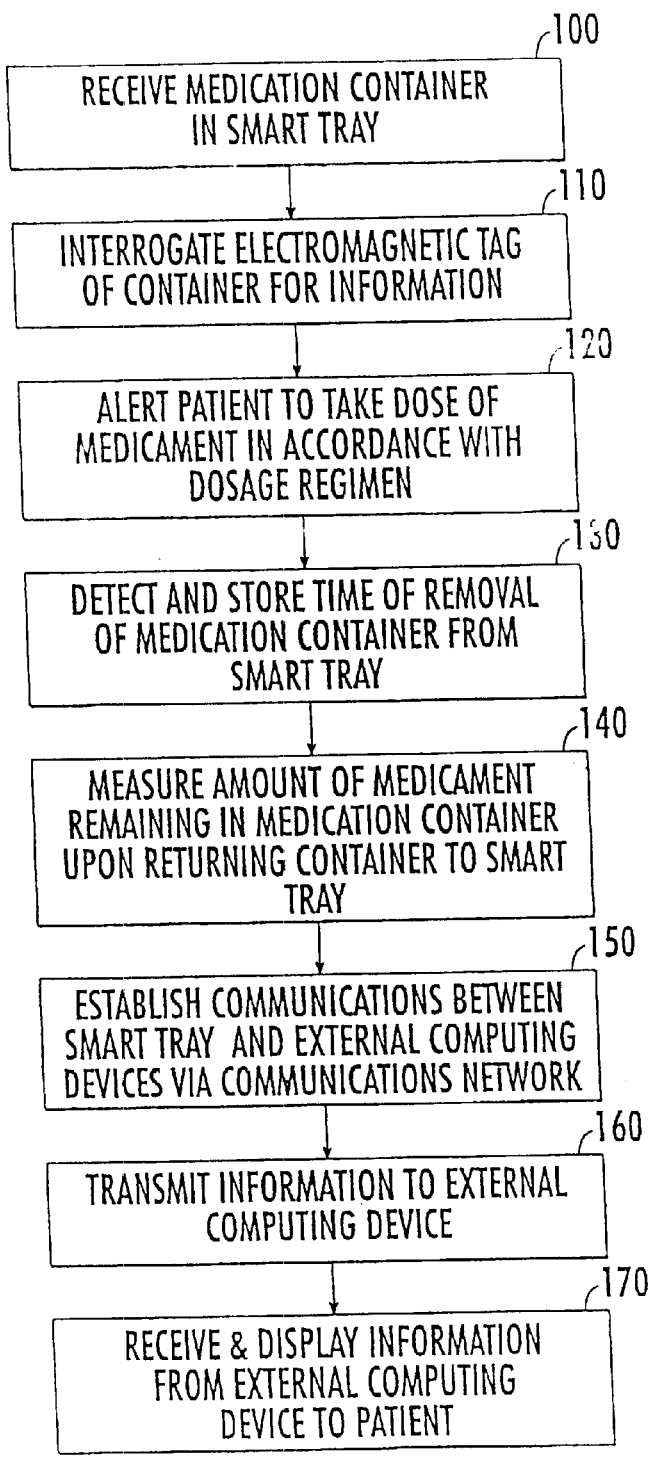
FIGS. 7–10 illustrate operations for monitoring compliance with medication regimens according to various aspects of the present invention.

Referring now to FIGS. 7–10, operations for monitoring patient compliance with medication treatment, according to various embodiments of the present invention, are illustrated. Referring initially to FIG. 7, a medication container containing one or more medicaments is removably received within a receptacle of a Smart Tray (Block 100). The container has an electromagnetic tag or other indicia associated therewith (e.g., attached thereto or embedded therein), such as an RFID tag, that may contain various types of information about the medicament(s) within the container. Exemplary information includes, but is not limited to, an identification of each medicament and dosage regimens for each medicament within the container.

The electromagnetic tag is interrogated by a reader, such as an RF coil, to retrieve information, such as an identification of the medicament(s) and/or a dosage regimen(s), from the electromagnetic tag (Block 110). A patient is then alerted via the Smart Tray to take a dose of a medicament in accordance with a dosage regimen associated with the identified medicament(s) (Block 120). Each time the patient removes the container from the receptacle, the time of removal may be detected by the reader and stored (Block 130).

A patient may be alerted by the Smart Tray to take a dose of the medicament(s) via visual and/or audio indicators. For example, a light may flash to indicate that a particular medicament is to be taken (and how much is to be taken). Similarly, an audio signal may sound to indicate that a particular medicament is to be taken (and how much is to be taken). Synthesized voice instructions also may be generated. In addition, a patient may be alerted via a display that displays messages.

Each time a container is returned to a receptacle, an amount of medicament(s) remaining in the container may be determined (Block 140). As described above, this step is preferably performed using piezoelectric elements or other weight sensors that deflect under the weight of the container and its contents.

According to another embodiment of the present invention, communications may be established between a Smart Tray and one or more external computing devices via a communications network (Block 150). Information may then be transmitted from the Smart Tray to the external computing device(s) (Block 160). For example, communications may be established with one or more healthcare providers that use data from the Smart Tray to determine whether a patient is in compliance with a medication (or other treatment) regimen. A healthcare provider can communicate with a patient by sending messages that can be displayed to a patient via the Smart Tray display (Block 170). In addition, a healthcare provider can modify a dosage regimen by transmitting commands to the Smart Tray. As another example, communications may be established with a medicament supplier such that additional medicament may be supplied to a patient.

In addition, a patient may establish communications with an external computing device via the Smart Tray, such as a Web site, and retrieve information therefrom (Block 170). For example, information about a particular medicament may be displayed to a patient, either via the Smart Tray or via a PC or Web TV in communication with the Smart Tray.

Figure 8:
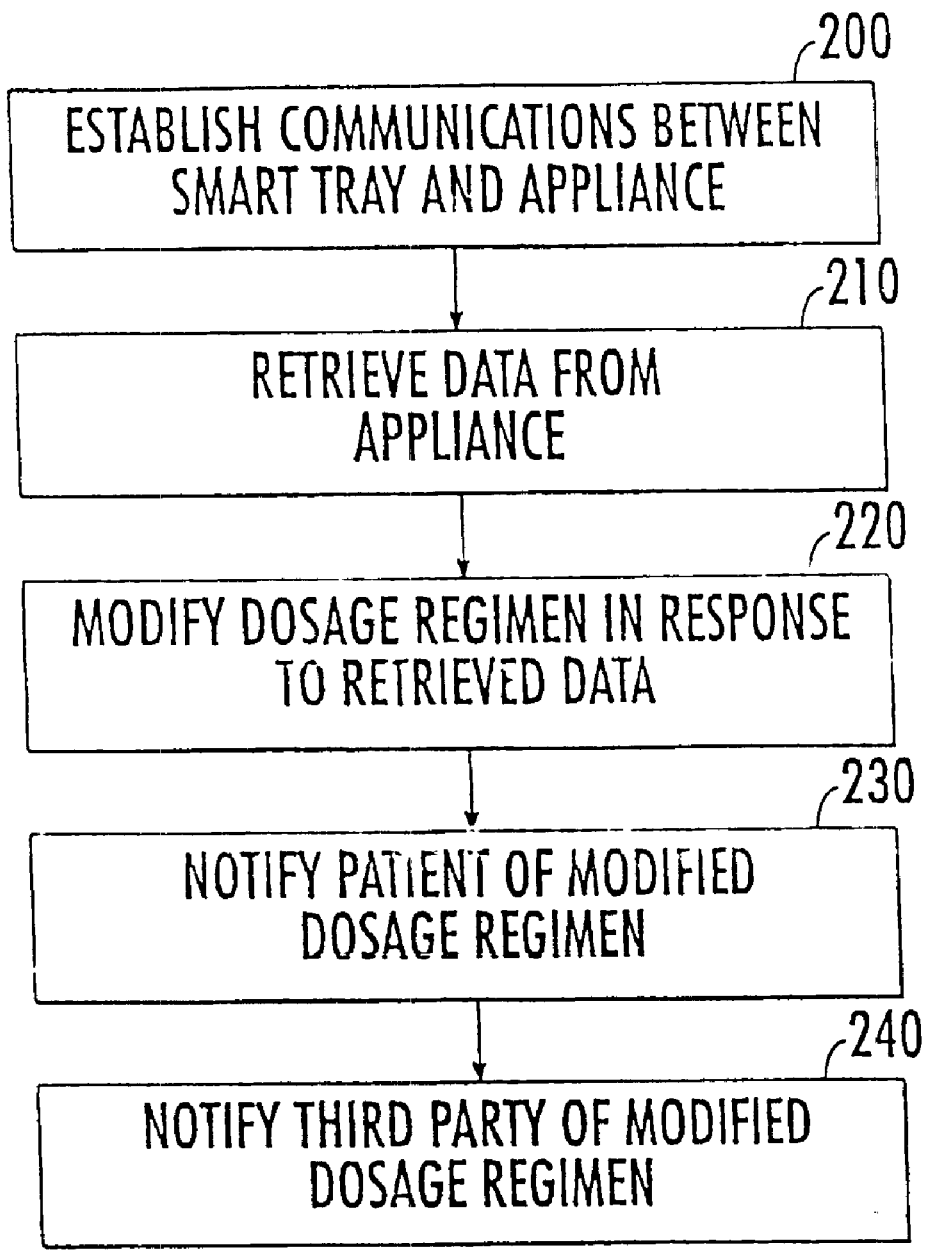

According to another embodiment of the present invention illustrated in FIG. 8, a Smart Tray can be configured to communicate with one or more appliances including, but not limited to, exercise devices, refrigerators, scanners, and weight scales. According to this embodiment, communications are established between a Smart Tray and an appliance (Block 200). Data is then retrieved from the appliance (Block 210). For example, a patient's weight is retrieved from a scale, or a patient's intake of sodium is retrieved from a "smart" refrigerator that monitors food obtained therefrom by the patient. A medication (or other) regimen associated with one or more medicaments can then be modified in response to data received from one or more of the appliances (Block 220).

A patient may be alerted by the Smart Tray of modified medication regimens (Block 230). In addition, third parties, such as healthcare providers, may be notified of modified medication regimens (Block 240). As described above, the Smart Tray may notify third parties by establishing communications with external computing devices and transmitting information therebetween.

Figure 9:
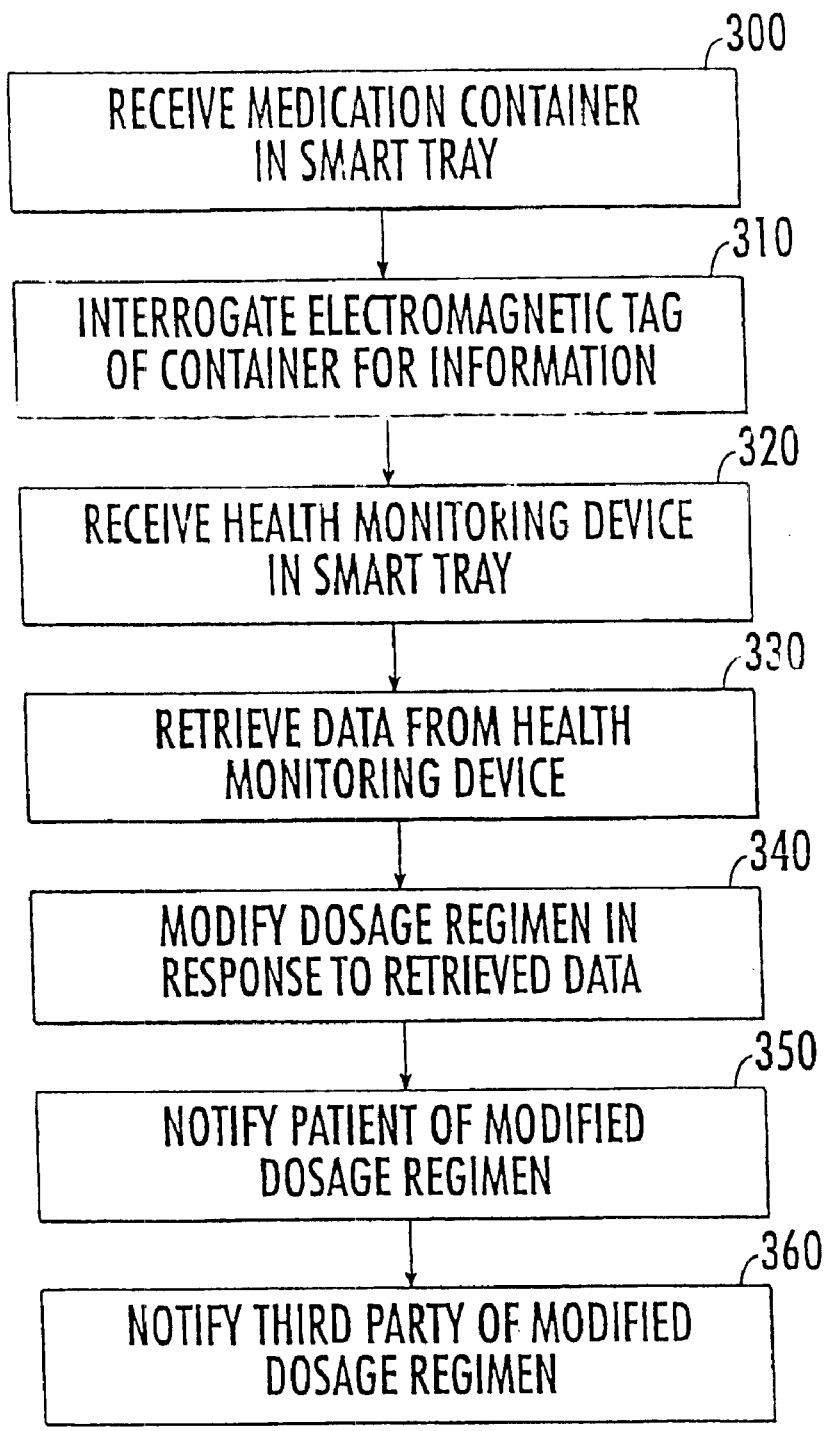

According to another embodiment of the present invention, a Smart Tray can be configured to modify a dosage regimen based upon data retrieved from a health monitoring device. Referring to FIG. 9, a medication container containing one or more medicaments is removably received within a receptacle of a Smart Tray (Block 300). The container has an electromagnetic tag associated therewith, as described above, that may contain various types of information about the medicament(s) within the container. The electromagnetic tag is interrogated by a reader, such as an RF coil, to retrieve information, such as an identification of the medicament(s) and/or dosage regimen(s), from the electromagnetic tag (Block 310).

A health monitoring device is placed within a receptacle (e.g., the sensing surface 37 described above) of a Smart Tray (Block 320). The health monitoring device has an electromagnetic tag attached thereto that identifies the health monitoring device. Data is then retrieved from the health monitoring device (Block 330). For example, the health monitoring device may be a blood pressure monitor that a patient has just used to measure his/her blood pressure. The patient places the blood pressure monitor within the receptacle and blood pressure data is retrieved by the Smart Tray.

A medication (or other) regimen associated with one or more medicaments can be modified in response to data received from a health monitoring device (Block 340). A patient may be alerted by the Smart Tray of modified medication regimens (Block 350). In addition, third parties, such as healthcare providers, may be notified of modified medication regimens (Block 360). As described above, the Smart Tray may notify third parties by establishing communications with external computing devices and transmitting information therebetween.

Figure 10:
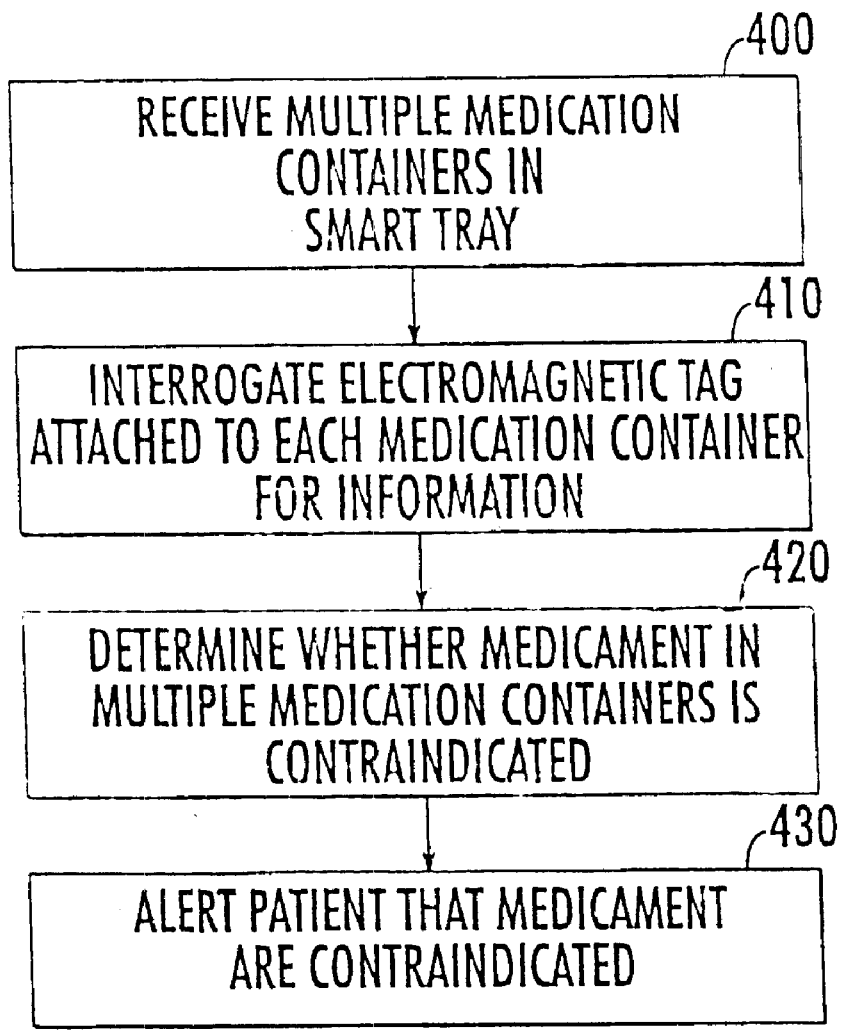

According to another embodiment of the present invention, a Smart Tray can be configured to determine whether two or more medicaments are contraindicated. Referring to FIG. 10, two or more medication containers are removably received within respective receptacles of a Smart Tray (Block 400). As described above, each medication container includes an electromagnetic tag or other identifier/indicator that contains various information about medicament(s) contained within the respective container. The electromagnetic tag of each container is then interrogated (Block 410) as described above. A determination is made, based on information retrieved from each respective electromagnetic tag, whether or not medicaments contained within the respective containers are contraindicated (Block 420). If two or more medicaments are determined to be contraindicated, a patient is alerted by the Smart Tray (Block 430). As described above, visual and/or audio signals may be utilized to alert a patient.

Tagging Persons and Medications

Figure 11:
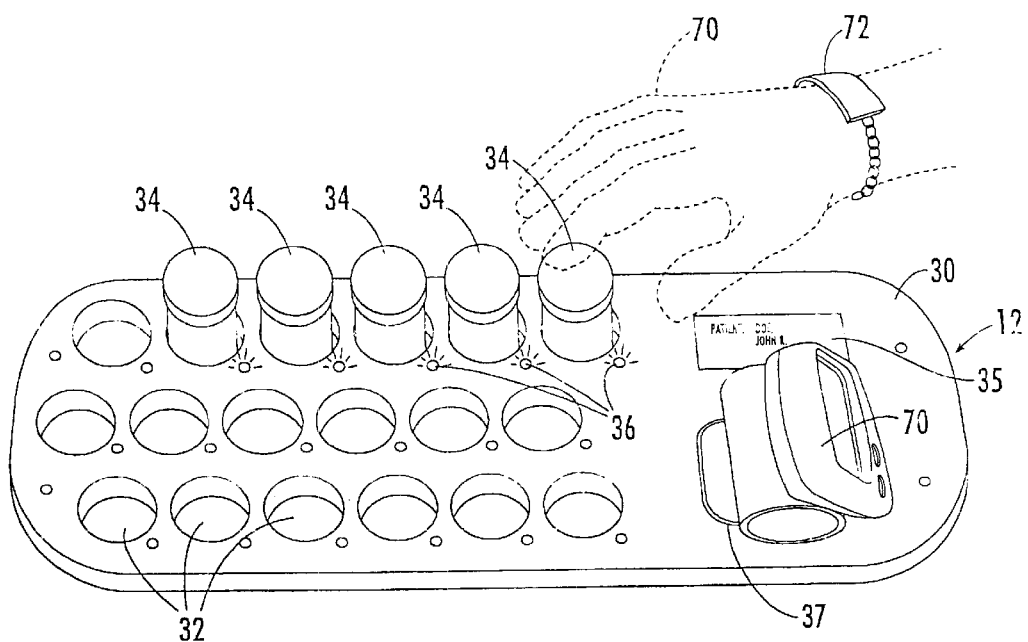
FIG. 11 illustrates a person having an identification tag attached thereto that allows a Smart Tray to identify the person when placing objects on the Smart Tray or when removing objects from the Smart Tray, according to another embodiment of the present invention.

According to additional embodiments of the present invention, persons and medications can be "tagged." In the illustrated embodiment of FIG. 11, a person 70 is wearing a bracelet 72. The bracelet 72 contains an identification tag that can be recognized by a sensor of the Smart Tray 12. Preferably, the identification tag is an electromagnetic tag, such as an RFID tag that can be interrogated by an RF coil array as described above. According to this embodiment, a Smart Tray 12 can identify a particular person that is placing or removing objects on the Smart Tray 12 or removing objects from the Smart Tray 12.

Figure 14:
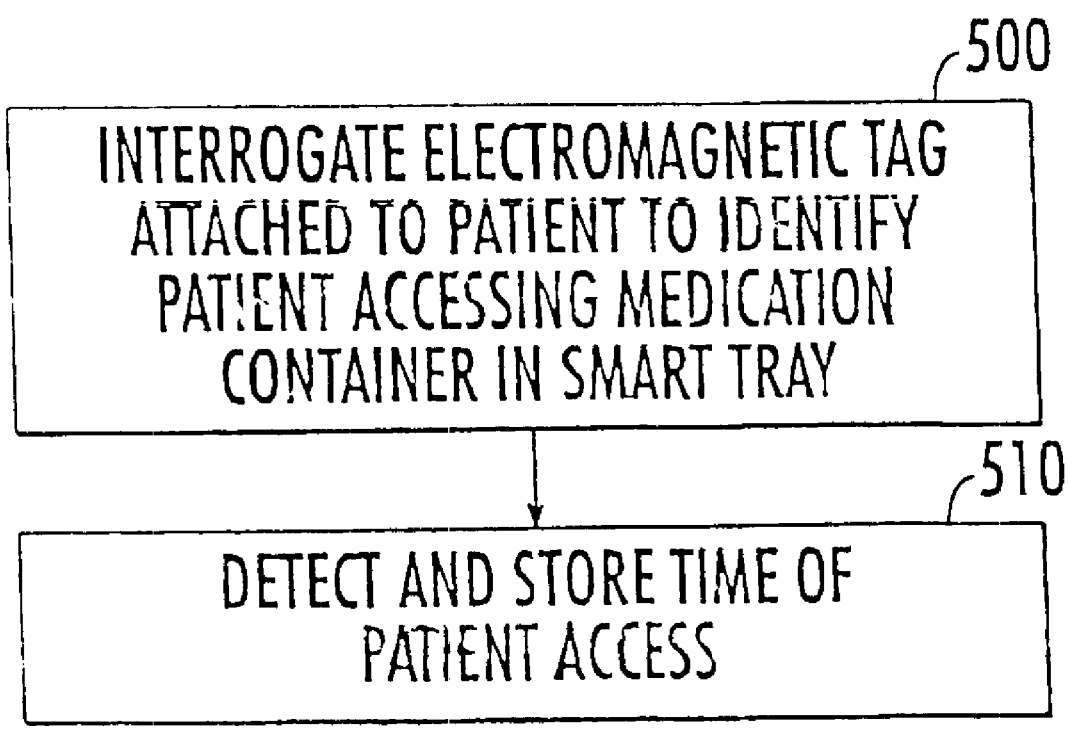
FIG. 14 illustrates operations for identifying a person tagged via an electromagnetic tag according to another embodiment of the present invention.

As illustrated in FIG. 14, a Smart Tray reader is configured to interrogate an electromagnetic tag, such as an RFID tag, attached to a person and retrieve information therefrom, such as the person's identity, when the person accesses an object on the Smart Tray (Block 500). The term "accessing" can mean placing a medication container on a Smart Tray and removing a medication container from a Smart Tray. In addition, the term "accessing" can mean placing on a Smart Tray and/or removing from a Smart Tray various other tagged objects including, but not limited to, blood pressure monitors and other monitoring devices. Preferably, a Smart Tray according to this embodiment of the present invention stores in the Smart Tray (or elsewhere) a time when a person accesses an object held by the Smart Tray (Block 510).

Figure 12:
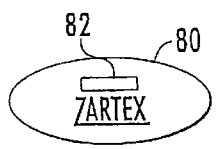
FIG. 12 illustrates a pill having an identifying tag or indicia attached thereto, according to another embodiment of the present invention.

Referring to FIG. 12, a comestible medicament 80 includes a non-toxic electromagnetic tag 82 thereon that allows a Smart Tray to identify the individual comestible medicament 80. The illustrated comestible medicament 80 is in pill form; however, it is understood that other types of comestible medicament forms may be utilized, such as caplets, capsules and the like. In addition, it is understood that a non-toxic electromagnetic tag may be disposed within a comestible medicament.

By tagging individual units of medication, a Smart Tray according to the present invention can accurately track whether a particular dose of a medication has been taken by a patient at a prescribed time. In addition, tagging individual medication units can facilitate control over medication inventories.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A comestible medicament comprising a non-toxic electromagnetic tag, wherein the electromagnetic tag contains information about the medicament including an identification of the medicament.

2. The comestible medicament according to claim 1 wherein the electromagnetic tag is a radio frequency identification (RFID) tag.

* * * * *